United States Patent [19]

Matz et al.

[11] Patent Number: 6,110,451
[45] Date of Patent: Aug. 29, 2000

[54] SYNERGISTIC COMBINATION OF CATIONIC AND AMPHOLYTIC POLYMERS FOR CLEANSING AND/OR CONDITIONING KERATIN BASED SUBSTRATES

[75] Inventors: Gary F. Matz, Carnegie, Pa.; Richard R. LaMar, Follansbee, W. Va.

[73] Assignee: Calgon Corporation, Pittsburgh, Pa.

[21] Appl. No.: 09/215,472

[22] Filed: Dec. 18, 1998

[51] Int. Cl.$^7$ .................................................. A61K 7/075
[52] U.S. Cl. ..................... 424/70.16; 424/70.17; 424/70.15; 424/70.19; 424/70.11
[58] Field of Search ................... 424/70.11, 70.122, 424/70.16, 43, 70.17, 401, 70.15; 510/122, 490

[56] References Cited

U.S. PATENT DOCUMENTS

| | | | |
|---|---|---|---|
| 4,591,610 | 5/1986 | Grollier et al. | 524/55 |
| 4,996,059 | 2/1991 | Grollier et al. | 424/71 |
| 5,750,099 | 5/1998 | Yoshihara et al. | 424/70.17 |
| 5,830,438 | 11/1998 | Dupuis | 424/45 |

FOREIGN PATENT DOCUMENTS

| | | | |
|---|---|---|---|
| 0791349A1 | 8/1997 | France | A61K 7/00 |
| 0531738A2 | 8/1992 | Japan | A61K 7/06 |

*Primary Examiner*—Yogendra Gupta
*Assistant Examiner*—Gregory E. Webb
*Attorney, Agent, or Firm*—Michael B. Martin; Thomas M. Breininger

[57] ABSTRACT

A keratin conditioning composition is disclosed that contains (a) a surfactant component that can contain anionic surfactants, amphoteric surfactants, cationic surfactants, nonionic surfactants and/or zwitterionic, (b) a water soluble, organic, ampholytic polymer conditioning agent, (c) a water soluble, organic, cationic polymer conditioning agent; (d) optionally a water insoluble liquid; and (e) an aqueous carrier. The conditioning composition optionally contains a silicone and/or an organic, water insoluble, liquid. The conditioning composition according to the present invention is useful in cleaning and/or conditioning keratin based substrates, such as hair, skin, and nails.

20 Claims, No Drawings

SYNERGISTIC COMBINATION OF CATIONIC AND AMPHOLYTIC POLYMERS FOR CLEANSING AND/OR CONDITIONING KERATIN BASED SUBSTRATES

FIELD OF THE INVENTION

The present invention relates to compositions containing surfactant and conditioning ingredients. The present invention also relates to methods for treating keratin based substrates, such as hair, skin and nails.

BACKGROUND OF THE INVENTION

Clean human hair quickly returns to its "dirty" condition due to contact with the environment and due to the buildup of the sebum secreted by the head. Within a short time (one day to a few days) hair begins to look and feel "dirty". In modern cultures, this look and feel is considered unacceptable requiring the wearer to shampoo their hair frequently. In some countries, the daily shampooing of hair is considered a normal requirement for proper hygiene, whether or not the hair has actually become "dirty".

Shampooing cleans the hair by the removal of environmental contaminants along with the sebum. However, shampooing removes natural oils and other moisturizing materials. If the hair is of significant length, the hair can be tangled and becomes unmanageable. Once dry, the hair has lost its shine and luster and can be dry and frizzy. Hair can also maintain a static charge when dry that results in "fly-away hair". If a shower is taken at the time of this shampooing, the natural oils etc. are also removed from the skin and nails.

As this hair problem has surfaced in the modern era, solutions have been developed to correct or to minimize the problem from frequent shampooing. The first acceptable solutions entailed the post-shampoo application of hair conditioners and hair rinses, generally while the hair is still wet immediately after shampooing. These conditioners and rinses were left on the hair for a period of time to allow sufficient treatment and then removed by rinsing with water. These solutions have, as late, been deemed inconvenient and time consuming. The solution to this problem has been the incorporation of conditioners into the shampoo itself, thus the advent of "conditioning shampoo".

Shampoos that contain conditioners or conditioning agents have not been completely satisfactory for various reasons. Hair is composed of keratin, a sulfur-containing fibrous protein. The isoelectric point of keratin, and more specifically of hair, is generally in the pH range of 3.2–4.0. Therefore, at the pH of a typical shampoo (about 5.5–6.5), hair carries a net negative charge. Consequently, cationic polymers due to their positive charge have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos containing good cleaning anionic surfactants, formation of highly surface active association complexes generally takes place, which imparts improved foam stability to the shampoo but provides poor conditioning. Maximum surface activity and foam stability, or lather, are achieved at near stoichiometric ratios of anionic surfactant: cationic polymer, where the complex is least water soluble. However, cationic conditioners exhibit some incompatibility at these ratios. Compatibility gives a commercially more desirable clear formulation, while incompatibility leads to a haze or precipitation, which is aesthetically less desirable in some formulations. Additionally when cationic surfactants are added as an ingredient in the shampoo, they do not provide optimal overall conditioning to the hair in the area of softness and tend to build up on the hair resulting in an unclean feel.

When various silicones are added to shampoos containing good cleaning anionic surfactants, improved conditioning properties are observed, however the silicones tend to build up on the hair after repeated shampoo application causing the hair to take on a greasy, unclean appearance.

Combinations of silicones and cationic polymers have been disclosed in an attempt to remedy the above mentioned shortcomings, but they fall short of delivering optimal conditioning properties while maintaining hair in a clean, ungreasy appearance after repeated shampoo applications.

Polyampholyte conditioning polymers have been disclosed that provide excellent wet conditioning properties, but these materials do not deliver the desired soft, shiny appearance to dry hair.

In spite of these attempts to provide optimal combinations of cleaning ability and hair conditioning, it remains desirable to provide further improved hair conditioning shampoo compositions. For instance, it remains desirable to improve overall conditioning, and especially shine and luster, wet and dry combing, and dry hair feel, of hair treated with shampoo containing conditioning materials. For shampoos containing oily materials in combination with cationic materials, it remains desirable to improve overall conditioning:, especially wet combing and detangling, dry combing, and dry hair feel. However merely increasing the level of one or both conditioning ingredients can result in adverse effects such as greasy hair feel and loss of fullness. It is desirable to improve conditioning without suffering from these drawbacks.

It is desirable to provide shampoo compositions and methods for cleaning and conditioning hair which can provide excellent cleaning performance and improved levels of conditioning while minimizing any adverse side effects associated with build-up due to the use of excess conditioning agent.

In addition to the above, the surface properties of human skin and nails are, of course, of basic interest in cosmetic science, and there has thus been a long-standing desire to discover compositions which will beneficially affect the topical condition of this keratinous substrate. Skin conditioning products are desired which will function to improve such properties as retention of skin moisture, softening of the skin, attraction of air moisture, retardation of skin water loss, reduction of fine lines and wrinkles, feel and reduction of skin irritations caused by contact with detergents, soaps and the like.

A desirable skin conditioner should impart all or some of the attributes of an emollient and a humectant, as well as provide improved lubricity and feel to the skin after treatment and/or reduce skin irritation caused by other components in the products such as soaps, detergents, foam boosters, surfactants, perfumes and the like.

There is an ongoing need to find new products for treating skin and nails that provide combinations of the above benefits.

SUMMARY OF THE INVENTION

The keratin conditioning composition of the present invention comprises:

(a) about 5% to about 50%, by weight, of a surfactant component selected from the group consisting of anionic surfactants, amphoteric surfactants, cationic surfactants, nonionic surfactants, and zwitterionic surfactants;

(b) about 0.05% to about 10%, by weight, of a water soluble, organic, ampholytic polymer;

(c) about 0.05% to about 10%, by weight, of a water soluble, organic, cationic polymer;

(d) zero to about 70%, by weight, of a water insoluble liquid; and (e) an aqueous carrier.

The method for treating keratin based substrates according to the present invention comprises contacting the substrate with the composition above.

DETAILED DESCRIPTION OF THE INVENTION

This invention provides a detersive surfactant containing liquid compositions that can provide both excellent cleaning performance and conditioning benefits to a wide variety of keratin containing substrates, including hair, skin, and nails. This is attained by forming a keratin conditioning composition that includes the surfactant, an aqueous carrier, a water soluble, organic ampholytic polymer conditioning agent, a water soluble, organic cationic polymer conditioning agent, and optionally, a silicone and/or organic, water insoluble oily liquid.

It has now been unexpectedly found that improved overall conditioning can be achieved by combining surfactant in the composition with a water soluble organic ampholytic polymer and a water soluble organic cationic polymer. Conditioning is also improved with the addition of a preferred optional water insoluble liquid component, that includes organic oily liquids and silicone.

These compositions can provide improved conditioning while reducing the level of undesirable side effects that can result from increasing the level of conditioning agent in prior known conditioning systems. As discussed previously, a conditioning agent system containing too much of a particular component can cause buildup on hair. Too much silicone can result in silicone build up on the hair over repeated usage and a loss of fullness of the hair. Too much organic liquid (oil) results in an oily feel and a loss of fullness of the hair. Too much conditioning agent results in a slick, oily feel of the hair. Now it has been found that combining these specific types of ingredients—surfactant, ampholytic polymers, cationic polymers, and the optional water insoluble liquid—can provide improved overall conditioning while minimizing the adverse effects of conditioning agent build-up that otherwise can occur upon increasing the levels of individual components in prior known conditioning systems. Furthermore, the use of ampholytic polymer in the compositions hereof can improve performance relative to similar systems with cationic polymers alone or in combination with silicone and/or organic water insoluble liquid conditioning agents.

The compositions and methods of the present invention have uses and applications on keratin based substrates other than hair. The composition of the present invention provides superior conditioning properties in skin and nail care products.

The composition comprising the combination of ampholytic polymer conditioning agent and cationic polymer conditioning agent of the present invention can improve the properties of various products other than shampoo, such diverse products include soap bars, dishwashing compositions, douches, hand and body lotions, suntan lotion, cold creams, preshave and after shave products, deodorant and antiperspirant products in stick, gel, lotion and aerosol foams, cosmetics including lipstick, rouge, mascara and eye liner, facial bases and powders, wrinkle and spot removing creams and lotions, and the like, and many other skin and nail care products.

Other materials can be included in such skin and nail care products. Hand and body lotions frequently contain emollients such as stearic acid, glycerol monostearate, mineral oil, glycerine, sesame oil, bees wax, lauryl, myristyl, cetyl and/or stearyl alcohols, lanolin, lecithin, sterols, isopropylmyristate, as well as many other recognized emollients. Emollients are typically used in the compositions of the present invention at levels of from about 1% to about 50% by weight.

The soap bar and dishwashing compositions of the present invention can contain all manner of anionic, nonionic, zwitterionic, amphoteric and/or cationic surfactants. Inherently bar soap is mostly anionic surfactant that is comprised of the water soluble reactant product of a fatty acid ester and an alkali. Typically, for liquid products, the surfactant will be present at from about 1% to about 50%, preferably about 3% to 35% by weight.

It has been found that by using compositions comprising the combination of ampholytic polymer conditioning agent and cationic polymer conditioning agent of the present invention, skin care products provide improved moisturization properties to the skin and allow the skin to feel smooth and lubricious.

The present invention provides keratin conditioning compositions such as a hair shampoo comprising: about 5% to about 50%, by weight, of component (a), about 0.05%, to about 10%, by weight, of component (b); about 0.05% to about 10%, by weight, of component (c); 0 to about 70%, by weight of component (d); and an aqueous carrier (e).

A preferred composition according to the present invention provides a keratin conditioning composition that comprises: about 5% to about 25%, more preferably about 10% to about 20%, by weight, of component (a), about 0.05%, to about 7%, more preferably about 0.05% to about 5%, by weight, of component (b); about 0.05% to about 4%, more preferably about 0.05% to about 3%, by weight, of component (c); 0 to about 50%, more preferably about 1% to about 50%, by weight of component (d); and an aqueous carrier (e).

A specific preferred hair shampoo composition according to the present invention comprises; (a) about 10 to about 15 weight % anionic surfactant and about 1 to about 5 weight % zwitterionic surfactant, (b) about 0.1 to about 1.5 weight % ampholytic polymer, and (c) about 0.1 to about 1.5 weight % cationic polymer (the remainder being water).

A specific preferred lotion composition according to the present invention is an oil in water emulsion which comprises; (a) about 3% to about 10%, by weight, nonionic surfactant; (b) about 0.1% to about 1%, by weight, ampholytic polymer; (c) about 0.1% to about 1% cationic polymer; (d) about 1% to about 25%, by weight, mineral oil; and (e) an aqueous carrier.

The optional water insoluble liquid can be organic or silicone and is preferably intermixed in, and is distributed throughout, the composition. The organic water insoluble liquid is generally selected from the group consisting of hydrocarbon oils and fatty esters. As used herein, "fatty ester" means esters having 10 or more carbon atoms.

The silicone conditioning agent is dispersed throughout the composition in the form of droplets or particles. Preferably, a suitable suspending agent is utilized to facilitate stability of the dispersed silicone.

As used herein, the terms "soluble" and "insoluble" used in reference to particular ingredients of the compositions refer to solubility or insolubility, respectively, of that ingredient in the claimed composition, unless otherwise specifically indicated. For example the terms "water soluble" and "water insoluble", as used herein, refer to solubility of the particular ingredient in water, as opposed to solubility in a composition such as shampoo.

All percentages are calculated by weight of the total composition unless otherwise specifically indicated. All ratios are weight ratios unless otherwise specifically indicated.

Ampholytic Polymer Conditioning Agent of (b)

The composition of the present invention comprises a water soluble, ampholytic organic polymer conditioning agent as an essential element. The polymeric ampholytic conditioning agent hereof will generally be present at levels of from about 0.05% to about 10% by weight preferably about 0.05% to about 5%, more preferably from about 0.1% to about 4%, with about 0.2% to about 3%, by weight, of the composition being most preferred. By "water soluble" ampholytic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The ampholytic organic polymers useful in the conditioning agent hereof are organic polymers that can provide conditioning benefits to keratin based substrates such as hair and skin and that are soluble in the composition, particularly in a shampoo compostion. Any ampholytic polymers which can provide these benefits can be used regardless of the charge density of the polymer.

The ampholytic polymer conditioning agent preferably comprises (A) at least one ethylenically unsaturated cationic monomer, (B) at least one ethylenically unsaturated acid containing monomer, and (C) about 0 to about 80 mol % of a monomer that is an ethylenically unsaturated nonionic monomer.

The water soluble, organic, ampholytic conditioning agent of the conditioning composition according the present invention is more preferably comprised of:

(A) about 1 to about 99 mol % of at least one monomer selected from the group consisting of alkyl acrylamidopropyl-dimethyl ammonium halides, alkyl methacrylamidopropyidimethyl ammonium halides, alkyl acryloyloxyethyl dimethyl ammonium halides, alkyl methacryloyloxyethyl dimethyl ammonium halides, and dialkyl diallyl ammonium halides;

(B) about 1 to about 99 mol % of an ethylenically unsaturated acid containing monomer selected from the group consisting of carboxylic acids and sulfonic acids, preferably at least one monomer selected from the group consisting of acrylic acid (AA), methacrylic acid (MAA), 2-acrylamido-2-methylpropane sulfonic acid (AMPSA) 2-methacrylamido-2-methylpropane sulfonic acid (MAMPSA), n-methacrylamidopropyl,n,n-dimethyl,amino acetic acid, n-acrylamidopropyl,n,n-dimethyl,amino acetic acid, n-methacryloyloxyethyl,n, n-dimethyl,amino acetic acid, and n-acryloyloxyethyl, n,n-dimethyl,amino acetic acid; and (C) about 0 to about 80 mol % of at least one monomer selected from the group consisting of $C_1$–$C_{22}$ straight or branched chain alkyl acrylate or methacrylate, a $C_1$–$C_{22}$ straight or branched chain n-alkyl acrylamide or methacrylamide, acrylamide methylacrylamide, n-vinylpyrrolidone, vinyl acetate or ethoxylated and propoxylated acrylate or methacrylate;

with a weight average molecular weight of, as determined by viscometry, of at least about 50,000.

The water soluble, organic, ampholytic polymer conditioning agents of the present invention are organic polymers which more preferably comprise:

(A) acrylamidopropyltrimethyl ammonium chloride (APTAC), methacrylamidopropyltrimethyl ammonium chloride (MAPTAC), acryloyloxyethyl trimethyl ammonium chloride (AETAC), methacryloyloxyethyl methyl sulfate (METAMS), methacryloyloxyethyl trimethyl ammonium chloride (METAC), or dimethyl diallyl ammonium chloride (DMDAAC);

(B) AA, MAA, AMPSA, and MAMPSA; and (C) optionally, a $C_1$–$C_{22}$ straight or branched alkyl acrylate or methacrylate, such as methyl, ethyl, butyl, octyl, lauryl, and stearyl acrylate esters, and methacrylate esters; acrylamide; methacrylamide; a $C_1$–$C_{22}$ straight or branched n-alkyl acrylamide or methacrylamide such as n-methyl, n-ethyl, n-butyl, n-octyl, t-octyl, n-lauryl, and n-stearyl acrylamides and methacrylamides.

The composition has a pH preferably between about pH 3 and about pH 9, more preferably from about pH 4 to about pH 8.

Preferably, the mol ratio of (A):(B) in said ampholytic polymer ranges from about 20:80 to about 95:5, more preferably from about 25:75 to about 75:25. Further, the weight average molecular weight of said polymer, as determined by viscometry, is preferably at least about 50,000, more preferably from about 100,000 to about 10,000,000, with a weight average molecular weight of about 150,000 to about 8,000,000 being most preferred. Alternatively, gel permeation chromatography (GPC) with light scattering detection can be used with approximately the same numbers.

The preferred polymers contain at least about 0.1 up to about 20 mol % of the above-defined acrylates, methacrylates, acrylamides, methacrylamides, vinyl acetate, vinyl alcohol and/or n-vinyl pyrrolidone. More preferably, the instant polymers contain about 5 to about 15 mol % of the acrylate, methacrylate, acrylamide, methacrylamide, vinyl acetate, vinyl alcohol and/or n-vinyl pyrrolidone moiety. In the most preferred case, methyl acrylate and/or acrylamide.

Optionally, but preferably, the instant polymers additionally contain, are further comprised of or are prepared using (C) up to about 80 mol percent, preferably at least about 0.1 mol percent, of a $C_1$–$C_{22}$ straight or branched chain alkyl acrylate or methacrylate, preferably a $C_1$–$C_4$ alkyl acrylate and most preferably methyl acrylate, a $C_1$–$C_{22}$ straight or branched chain n-alkyl acrylamide or methacrylamide, preferably a $C_1$–$C_4$ alkyl acrylamide and most preferably acrylamide, wherein the upper mol percent of (C) in the instant polymers is limited by solubility considerations. The ampholytic polymer is preferably comprised of about 1 to about 40 mol %, more preferably about 1 to about 35 mol %, of (C), (C) being a monomer that is preferably selected from the group consisting of $C_1$–$C_{22}$ acrylate esters, $C_1$–$C_{22}$ methacrylate esters, acrylamide, and $C_1$–$C_{22}$ n-alkyl acrylamides.

Preferably, the monomers of (C) are selected from the group consisting of (i) $C_1$–$C_{22}$ acrylate esters which are selected from the group consisting of methyl, ethyl, butyl, octyl, lauryl, and stearyl acrylate esters; (ii) $C_1$–$C_{22}$ methacrylate esters which are selected from the group consisting of methyl, ethyl, butyl, octyl, lauryl, and stearyl methacrylate esters; and (iii) $C_1$–$C_{22}$ n-alkyl acrylamides which are selected from the group consisting of n-methyl, n-ethyl, n-butyl, n-octyl, t-octyl, n-lauryl, and n-stearyl acrylamides and methacrylamides.

Specific preferred examples of the ampholytic polymer conditioning agent according to the present invention include (1) a polymer comprised of about 45 mol % MAPTAC, about 45 mol % acrylic acid, and about 10 mol % methylacrylate and (2) a polymer comprised of about 30 mol % DMDAAC, about 35 mol % acrylic acid, and about 35 mol % acrylamide. These polymers are available from Calgon Corporation as MERQUAT® 2001 and MERQUAT® plus 3330, respectively.

Cationic Polymer Conditioning Agent of (c)

The composition of the present invention comprises a water soluble organic cationic polymer conditioning agent as an essential element. The polymeric cationic conditioning agent hereof will generally be present at levels of from about 0.05% to about 10% by weight preferably about 0.05% to about 5%, more preferably from about 0.1% to about 4%, with about 0.2% to about 3%, by weight, of the composition being most preferred. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration. The minimum amount of this cationic polymer conditioning agent that is yet sufficient to provide the desired results, without an excess, is preferred. Thus, the lower amounts are generally preferred.

The cationic organic polymers useful in the conditioning agent hereof are organic polymers that can provide conditioning benefits to hair and other keratin based substrates, and that are soluble in the composition. Any cationic polymers which can provide these benefits can be used regardless of the cationic charge density of the polymer.

Amongst the cationic polymers which can be used according to the present invention, the following are specific examples:

(1) Quaternary derivatives of cellulose ethers.
(2) Quaternary derivatives of guar.
(3) Homopolymers and copolymers of dimethyl diallyl ammonium chloride (DMDAAC).
(4) Homopolymers and copolymers of methacrylamidopropyl trimethyl ammonium chloride (MAPTAC).
(5) Homopolymers and copolymers of acrylamidopropyl trimethyl ammonium chloride (APTAC).
(6) Homopolymers and copolymers of methacryloyloxyethyl trimethyl ammonium chloride (METAC).
(7) Homopolymers and copolymers of acryloyloxyethyl trimethyl ammonium chloride (AETAC).
(8) Homopolymers and copolymers of methacryloyloxyethyl trimethyl ammonium methyl sulfate (METAMS).
(9) Quaternary derivatives of starch.

The water soluble, organic, cationic polymer conditioning agents of the present invention are organic polymers which more preferably comprise:

(1) The polymeric quaternary ammonium salt of hydroxyethyl cellulose reacted with a trimethyl ammonium substituted epoxide referred to as Polyquaternium-10 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(2) The quaternary ammonium derivative of hydroxypropyl guar referred to as guar hydroxypropyltrimonium chloride in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(3) The copolymer of hydroxyethylcellulose and DMDAAC referred to as Polyquaternium-4 in the *International Cosmetic Ingredient Dictionary* published by the Cosmetic, Toiletry, and Fragrance Association (CFTA), 1101 17th Street, N.W., Suite 300, Washington, D.C. 20036.

(4) The copolymer of acrylamide and METAMS referred to as Polyquaternium-5 in the *International Cosmetic Ingredient Dictionary* published by the Cosmetic, Toiletry, and Fragrance Association (CFTA), 1101 17th Street, N.W., Suite 300, Washington, D.C. 20036.

(5) The homopolymer of DMDAAC referred to as Polyquaternium-6 in the *International Cosmetic Ingredient Dictionary* published by the Cosmetic, Toiletry, and Fragrance Association (CFTA), 1101 17th Street, N.W., Suite 300, Washington, D.C. 20036.

(6) The copolymer of acrylamide and DMDAAC referred to as Polyquaternium-7 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(7) The copolymer of vinyl pyrrolidone and METAMS referred to as Polyquaternium-11 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(8) The homopolymer of METAMS referred to as Polyquaternium-14 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(9) The copolymer of methacrylamide and METAMS referred to as Polyquaternium-15 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(10) The polymeric quaternary ammonium salt of hydroxyethyl cellulose reacted with a lauryl dimethyl ammonium substituted epoxide referred to as Polyquaternium-24 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(11) The copolymer of vinyl pyrrolidone and MAPTAC referred to as Polyquaternium-28 in the *International Cosmetic Ingredient Dictionary* published by the Cosmetic, Toiletry, and Fragrance Association (CTFA), 1101 $17^{th}$ Street, N.W., Suite 300, Washington, D.C. 20036.

(12) The copolymer of acrylamide and METAC referred to as Polyquaternium-32 in the *International Cosmetic*

Ingredient Dictionary published by the Cosmetic, Toiletry, and Fragrance Association (CTFA), 1101 17$^{th}$ Street, N.W., Suite 300, Washington, D.C. 20036.

(13) The copolymer of acrylamide and AETAC referred to as Polyquaternium-33 in the *International Cosmetic Ingredient Dictionary* published by the Cosmetic, Toiletry, and Fragrance Association (CTFA), 1101 17$^{th}$ Street, N.W., Suite 300, Washington, D.C. 20036.

(14) The copolymer of butylmethacrylate, dimethylaminoethylmethacrylate and METAMS referred to as Polyquaternium-36 in the *International Cosmetic Ingredient Dictionary* published by the Cosmetic, Toiletry, and Fragrance Association (CTFA), 1101 17$^{th}$ Street, N.W., Suite 300, Washington, D.C. 20036.

(15) The homopolymer of METAC referred to as Polyquaternium-37 in the *International Cosmetic Ingredient Dictionary* published by the Cosmetic, Toiletry, and Fragrance Association (CTFA), 1101 17$^{th}$ Street, N.W., Suite 300, Washington, D.C. 20036.

(16) The copolymer of METAMS, methyl methacrylate and hydroxyethylmethacrylate referred to as Polyquaternium-45 in the *International Cosmetic Ingredient Dictionary* published by the Cosmetic, Toiletry, and Fragrance Association (CTFA), 1101 17$^{th}$ Street, N.W., Suite 300, Washington, D.C. 20036.

(17) The homopolymer of MAPTAC referred to as polymethacrylamidopropyltrimonium chloride in the *International Cosmetic Ingredient Dictionary* published by the Cosmetic, Toiletry, and Fragrance Association (CTFA), 1101 17$^{th}$ Street, N.W., Suite 300, Washington, D.C. 20036.

(18) Hydroxypropyl trimethyl ammonium chloride ether derivatives of starch, as generally described by the CAS Registry Number 5670-58-6. The starch of which can be derived from a variety of natural sources such as corn, potato, rice, tapioca, wheat, or other sources.

Specific preferred examples of the cationic polymer conditioning agent according to the present invention include the polymeric quaternary ammonium salts of hydroxyethyl cellulose reacted with a trimethyl ammonium substituted epoxide, the quaternary ammonium derivatives of hydroxypropyl guar, and the quaternary ammonium derivatives of starches.

As discussed above, the ampholytic and cationic polymers hereof are water soluble. This does not mean, however, that it must be soluble in the present composition such as a shampoo composition. Preferably however, the polymers are either soluble in the present composition, or in a complex coacervate phase in the composition formed by the ampholytic and cationic polymers and other ionic materials. Complex coacervates of the ampholytic and cationic polymers can be formed with anionic surfactants, amphoteric surfactants, zwitterionic surfactants, cationic surfactants.

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, for example, J. Caelles, et al. "Anionic and Cationic Compounds in Mixed Systems", *Cosmetics & Toiletnes*, Vol. 106, April 1991, pp. 49–54, C. J. van Oss, "Coacervation, Complex Coacervation and Flocculation", *J. Dispersion Science and Technology*, Vol. 9 (5,6), 1988–89, pp. 561–573, and D. J. Burgess, "Practical Analysis of Complex Coacervate Systems", *J. of Colloid and Interface Science*, Vol.: 140, No. 1, November 1990, pp. 227–238.

It is believed to be particularly advantageous for the ampholytic and cationic polymer to be present in, say the shampoo composition in a coacervate phase, or to form a coacervate phase upon application or rinsing of the composition to or from the substrate. Complex coacervates are believed to more readily deposit on the keratin based substrate. Thus, in general, it is preferred that the ampholytic and cationic polymers exist in the composition as a coacervate phase or form a coacervate phase upon dilution. If not already a coacervate in the composition, the ampholytic and cationic polymers will preferably exist in a complex coacervate form in the composition upon dilution with water to a water:composition weight ratio of about 20:1, more preferably at about 10:1, even more preferably at about 8:1.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

The total of (b) and (c) in the composition of the present invention is preferably no more than about 10 weight %, preferably no more than about 5%, more preferably no more than about 2%, with a weight % of no more than 1 being most preferred. Higher amounts of these two polymer conditioning agents provides more conditioning. However, as this amount rises above 1% by weight up to and over 10% by weight the slightly added conditioning does not justify the significant increase in cost to the resulting product.

The preferred combinations of the polymer conditioning agents of the present invention include for (b) the ampholytic polymers of (1) a polymer comprised of about 45 mol % MAPTAC, about 45 mol % acrylic acid, and about 10 mol % methylacrylate and (2) a polymer comprised of about 30 mol % DMDAAC, about 35 mol % acrylic acid, and about 35 mol % acrylamide (MERQUAT® 2001 and MERQUAT® plus 3330); for (c) a combination with one or more of; the polymeric quaternary ammonium salts of hydroxyethyl cellulose reacted with a trimethyl ammonium substituted epoxide (UCARE Polymer JR, Amerchol), the quaternary ammonium derivatives of hydroxypropyl guar (Jaguar, Rhodia), and the quaternary ammonium derivatives of starches.

Exemplary complex coacervate shampoo compositions are shown in the examples.

Surfactant Component of (a)

Anionic Surfactant

The conditioning compositions of the present invention preferably contain an anionic surfactant as at least part of component (a), which can comprise one or more anionic detersive surfactants which are anionic at the pH of the composition, to provide cleaning performance to the composition.

The anionic surfactant of component (a) can be the only surfactant and will generally be present at a level from about 2% to about 50%, preferably from about 5% to about 30%, more preferably from about 6% to about 25%, of the composition, with about 10% to about 15% being most preferred. For cleansing compositions, the anionic surfactant is the preferred surfactant and is preferably present in the composition in combination with a second surfactant that is not cationic.

Anionic detersive surfactants useful herein include those that are disclosed in U.S. Pat. No. 5,573,709, the disclosure of which is incorporated herein by reference in its entirety. Examples include alkyl and alkyl ether sulfates. Specific examples of alkyl ether sulfates which may be used In the present invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic detersive surfactants are the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfated $C_{12-38}$ n-paraffins.

Additional examples of synthetic anionic detersive surfactants which come within the terms of the present invention are the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfofosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Many additional synthetic anionic surfactants are described in McCutcheon's. Emulsifiers and Detergents, 1989 Annual, published by M. C. Publishing Co., which is incorporated herein by reference in its entirety. Also V.S. U.S. Pat. No. 3,929,678, Laughlin et al., issued Dec. 30, 1975, discloses many other anionic as well as other surfactant types and is incorporated herein by reference in its entirety.

Preferred anionic detersive surfactants for use in the present compositions include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine 1 lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactant

The keratin conditioning composition of the present invention preferably contains an amphoteric detersive surfactants. The amount of this surfactant is preferably no more than about 10 weight %. Examples of amphoteric detersive surfactants which can be used in the compositions of the present invention are those which are broadly described as derivatives of aliphatic secondary and tertiary amines in which the aliphatic substituent contains from about 8 to 18 carbon atoms and one contains an anionic water solubilizing group e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ as described in U.S. Pat. No. 2,528,378.

Optional Detersive Surfactants

In addition to the anionic detersive surfactant component, the compositions of the present invention can optionally contain other detersive surfactants. These include nonionic surfactants, and zwitterionic surfactants. Optional detersive surfactants, when used, are typically present at levels of from about 0.5% to about 20%, more typically from about 1% to about 10%, although higher or lower levels can be used. The total amount of detersive surfactant in compositions containing optional detersive surfactants in addition to the anionic surfactant will generally be from about 5% to about 40%, preferably from about 8% to about 30%, more preferably from about 10% to about 25%. Cationic detersive surfactants can also be used, but are generally less preferred because they can adversely interact with the anionic detersive surfactant. Cationic detersive surfactants, if used, are preferably used at levels no greater than about 5%. Cationic surfactants, if used, are more typically conditioning agents which can optionally be included in the compositions hereof.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are: The long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Preferred compositions of the present invention are shampoos and these preferably contain combinations of anionic surfactants with zwitterionic surfactants and/or amphoteric surfactants. Especially preferred shampoos contain from about 0% to about 16% of alkyl sulfates, from 0% to about 16% of ethoxylated alkyl sulfates, and from about 0% to about 10% of optional detersive surfactants selected from the nonionic, amphoteric, and zwitterionic detersive surfactants, with at least 5% of either alkyl sulfate, ethoxylated alkyl sulfate, or a mixture thereof, and a total surfactant level of from about 10% to about 25%.

Optional Water Insoluble Liquids of (d)

Optional Organic Water Insoluble Liquid

The compositions of the present invention optionally contain a nonvolatile, water insoluble, organic, oily liquid as a preferred type of conditioning agent. The conditioning oily liquid can protect, lubricat, and/or moisturize the skin and add shine, softness, and luster to the hair. Additionally, it can also enhance dry combing and dry hair feel. The hair conditioning oily liquid is typically present in the compositions at a level of from about 0.05% to about 5%, by weight of the composition, preferably from about 0.2% to about 3%, more preferably from about 0.5% to about 1%.

For skin care formulations, oil in water emulsions will contain amounts, by weight, of the organic insoluble liquid of about 3 to about 25%, preferably about 5 to about 20%, with about 6 to 15% being most preferred. Water in oil skin care formulations will contain amounts, by weight, of the organic insoluble liquid of about 25 to about 70%, preferably about 30 to about 60%, with about 35 to about 50% being most preferred.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The conditioning oily liquids hereof generally will have a viscosity of about 3 million cs or less, preferably about 2 million cs or less, more preferably about 1.5 million cs or less.

The conditioning oily materials hereof are liquids selected from the group consisting of hydrocarbon oils and fatty esters. The fatty esters hereof are characterized by having at least 12 carbon atoms, and include esters with hydrocarbon chains derived from fatty acids or alcohols, e.g., monoesters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably-contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general The branched chain polymers can have substantially higher chain length. The number average molecular weight of such materials can vary widely but will typically be up to about 500, preferably from about 200 to about 400, more preferably from about 300 to about 350.

Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and undecane, such as 2, 2, 4, 4, 6, 6, 8, 8-dimethyl-10-methylundecane and 2, 2, 4, 4, 6, 6-dimethyl-8-methyinonane, sold by Permethyl Corporation. A preferred hydrocarbon polymer is polybutene, such as the copolymer of isobutylene and butene. A commercially available material of this type is L-19 polybutene from Amoco Chemical Co. (Chicago, Ill., USA)

Monocarboxylic acid esters hereof include esters of alcohols and/or acids of the formula R' COOR wherein alkyl or alkenyl radicals and the sun of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyl stearate, diisopropyl adipate, and tristearyl citrate. Polyhydric alcohol esters include alkylene glycol esters, for and di-fatty acid esters, diethylene example ethylene glycol mono glycol mono- and di-fatty acid esters, polyethylene glycol mono and di-fatty acid esters, propylene glycol mono- and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cotton seed oil, corn oil, olive oil, cod liver oil, almond oil, avocado oil, palm oil, sesame oil, lanolin and soybean Synthetic oils include triolein and tristearin glyceryl dilaurate. Preferred glycerides are di-, and tri-glycerides. Especially preferred are triglycerides.

Optional Silicone Conditioning Agent

The compositions of the present invention optionally contain a nonvolatile, nonionic silicone conditioning agent which is insoluble in the compositions hereof. The silicone conditioning agent is intermixed in the composition so as to be in the form of dispersed, insoluble particles, or droplets. The silicone conditioning agent comprises a nonvolatile, insoluble, silicone fluid and optionally comprises a silicone gum which is insoluble in the composition as a whole but is soluble in the, silicone fluid. The silicone conditioning agent can also comprise other ingredients, such as a silicone resin to enhance deposition efficiency.

The silicone conditioning agent may comprise low levels of volatile silicone components; however, such volatile silicones will preferably exceed no more than about 0.5%, by weight, of the composition. Typically, if volatile silicones are present, it will be incidental to their use as a solvent or carrier far commercially available forms of other ingredients, such as silicone gums and resins The silicone conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate test method CTM0004, Jul. 20, 1970.

The silicone conditioning agent will be used in the compositions hereof at levels of from about 0.5% to about 10% by weight of the composition, preferably from about 0.1% to about 10%, more preferably from about 0.5% to about 8%, most preferably from about 0.5% to about 5%. The silicone conditioning agent is also preferably used in combination with the organic water insoluble liquid.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicones fluids having conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

The nonvolatile polyalkylsiloxane fluids that may be used include, for example, polydimethyl siloxanes. These siloxanes are available, for example, from the General Electric Company in their Viscasil® and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

References disclosing suitable silicone fluids include U.S. Pat. No. 2,826,551, Geen; U.S. Pat. No. 3,964,500, Drakoff, issued Jun. 22,1976; U.S. Pat. No. 4,364,837, Pader; U.S Pat. No. 5,573,709, Wells; British Patent 849,433, Woolston; and PCT Patent Application WO93/08787. All of these patents are incorporated herein by reference in their entireties. Also incorporated herein by reference is *Silicon Compounds* distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethyl siloxane) (methylvinylsiloxane) copolymer, poly(dimethyl siloxane) (diphenyl siloxane)(methylvinylsiloxane) copolymer and mixtures thereof.

Preferably the silicone conditioning agent comprises a mixture of a polydimethylsiloxane gum, having a viscosity greater than about 1,000,000 centistokes and polydimethyl siloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0 Silanes used in the manufacture of silicone resins include monomethyl-, dimethyl-, trimethy-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicones resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in *Encyclopedia of Polymer science and Engineering*, Volume 15, Second Edition, pp. 294–308, John Wiley & Sons, Inc., 1989, incorporated herein by reference.

Examples of the more preferred optional silicones used include, dimethicone, cyclomethicone, trimethyl silyl amodimethicone, phenyl trimethicone, trimethyl siloxy silicate, polyorganosiloxane, polyalkylsiloxane, polyarylsiloxane, polyalkylarylsiloxane, and polyestersiloxane copolymers.

Aqueous Carrier (e)

The compositions of the present invention are typically liquids which, preferably, are pourable at room temperature. The compositions hereof will comprise an aqueous carrier, i.e., water, which will generally be present at a level of about 20% to about 95% by weight of the composition, preferably from about 60% to about 85% for pourable, liquid formulations such as shampoos, shower gels, liquid hand-soaps, and lotions. The compositions of the present invention can also be in other forms, such as gels, mouse, etc. In such cases, appropriate components known in the art such as gelling agents (e.g., hydroxyethyl cellulose), etc. can be included in the compositions. Gels will typically contain from about 20% to about 90% water. Mousses will be a low viscosity composition and will be packaged as a sprayable liquid according to techniques well known in the art, typically in an aerosol canister including a propellant or a means for generating an aerosol spray.

Optional Components

The present compositions may also comprise a variety non-essential, optional components suitable for rendering such compositions more cosmetically or aesthetically acceptable or to provide them with additional usage benefits. A variety of such are known to those skilled in the art in hair, skin and nail care. These ingredients are well-known and include without limiting the invention thereto: pearlescent aids, such as coated mica, ethylene glycol distearate; opacifiers, such as Tin,; preservatives, such as 1,2-dibromo-2,4-dicyano butane (MERGUARD®, Calgon Corporation, Pittsburgh, Pa., USA), benzyl alcohol, 1,3-bis (hydroxymethyl)-5, 5-dimethyl-2,3-imidazolidinedione (e.g., GLYDANT®, Lonza Inc., Fairlawn, N.J., USA), methylchloroisothiazolinone (e.g., KATHON®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate (EDTA).

Another optional ingredient that can be advantageously used is an anti-static agent. The anti-static agent should not unduly interfere with the in-use performance and end-benefits of the composition. This is more important for shampoo compositions and, the anti-static agent should particularly not interfere with the anionic detersive surfactant. Suitable anti-static agents include, for example, tricetyl methyl amnonium chloride.

Typically, from about 0.1% to about 5%; of such anti-static agent is incorporated into the shampoo compositions.

Though the polymer components may act to thicken the present compositions to some degree, the present compositions may also optionally contain other thickeners and viscosity modifiers such as an ethanolamide of a long chain fatty acid, such as polyethylene (3) glycol lauramide and coconut monoethanolamide (cocamide MEA), ammonium xylene sulfonate, xanthan gum, and hydroxyethyl cellulose.

These optional components generally are used individually in the compositions of the present invention at a level of from about 0.01% to about 10%, preferably from about 0.05% to about 5.0% of the composition.

Method of Use

The compositions of the present invention are utilized conventionally, i.e., the hair or skin is shampooed or washed by applying an effective amount of the composition to the scalp or skin, and then rinsing it off with water. Application of the shampoo to the scalp in general, encompasses messaging or working the shampoo in the hair such that all or most of the hair on the scalp is contacted. The term an "effective amount" as used herein, is an amount which is effective in cleaning and conditioning the keratin substrate. Generally, from about 1 g to about 20 g of the composition is applied for cleaning and conditioning the hair, preferably, the shampoo is applied to hair in a wet or damp state.

The compositions hereof can also be useful for cleaning and conditioning the skin. For such applications, the composition would be applied to the skin in a conventional manner, such as by rubbing or massaging the skin with the composition, optionally in the presence of water, and then rinsing it away with water. In the case of non-rinse-off products, the composition is left in full concentration in contact with the skin.

EXAMPLES

The following examples illustrate the present invention. It will be appreciated that other modifications of the present invention within the skill of those in the hair, skin or nail care formulation art can be undertaken without departing from the spirit and scope of this invention.

All parts, percentages, and ratios herein are by weight unless otherwise specified. Some components may come from suppliers as dilute solutions. The levels given reflect the weight percent of the active material, unless otherwise specified.

The following Examples 1–3 are a shampoo compositions, with Example 3 being one according to the present invention.

Examples 1–3

The following shampoo formulations demonstrate the synergistic benefit found when ampholytic polymer Polyquaternium-47 is used with cationic polymer Polyquaternium-10.

| Ingredient | INCI Name | % Active For Examples 1–3 | | |
|---|---|---|---|---|
| | | EX. 1 | EX. 2 | EX. 3 |
| Water | Water | q.s. to 100 for all | | |
| MERQUAT 2001[1] | Polyquaternium-47 | 0.26 | — | 0.13 |
| UCARE Polymer JR ® 400[2] | Polyquaternium-10 | — | 0.26 | 0.13 |
| Standapol ® A[3] | Ammonium Lauryl Sulfate | 2.1 | 2.1 | 2.1 |
| Standapol ® EA-3[3] | Ammonium Laureth Sulfate | 4.7 | 4.7 | 4.7 |
| Tegobetaine ® L-7[4] | Cocamidopropyl betaine | 1.5 | 1.5 | 1.5 |
| Monamid ® 1113[5] | Cocamide DEA | 3.0 | 3.0 | 3.0 |
| Tween ® 20[6] | Polysorbate 20 | 1.0 | 1.0 | 1.0 |
| Citric Acid | Citric Acid | q.s. to pH 6.0 for all | | |
| Sodium Chloride | Sodium Chloride | 0.75 | 0.75 | 0.75 |
| MERGUARD ®[1] 1200 | Methyldibromo Glutaronitrile (and) Phenoxyethanol | 0.2 | 0.2 | 0.2 |

[1]From Calgon Corporation
[2]From Amerchol
[3]From Henkel
[4]From Goldschmidt Chemical
[5]From Mona
[6]From ICI The shampoos from Examples 1–3 were evaluated for wet hair combing using the Dia-Stron Mini Tensile Tester, Dia-Stron Limited, Andover, Hampshire, U.K. The amount of work in milli Joules (mJ) required to comb the hair is measured directly. Lower work levels indicate superior conditioning as the hair is easier to comb.

| Shampoo | Total Work (mJ) |
|---|---|
| Example 1 | 35.5 |
| Example 2 | 91.9 |
| Example 3 | 26.7 |

The synergistic properties were evaluated by determining the reduction in total work found with the combination compared with what would be expected from each polymer individually. The method for calculating K value is well known to those skilled in the art. In this example, the K value was determined by the following formula:

$$\text{Ratio} = \frac{[\text{mJ for PQ10}/2] + [\text{mJ for PQ47}/2]}{[\text{mJ for combination}]}$$

where "[mJ for PQ10/2]" means the total work in mJ observed when Polyquaternium-10 is used at full concentration (0.26% w/w) divided by 2 because the combination is made up of ½ Polyquaternium-10;
  "[mJ for PQ47/2]" means the total work in mJ observed when Polyquaternium-47 is used at full concentration (0.26% w/w) divided by 2 because the combination is made up of ½ Polyquaternium 47;
  and "[mJ for combination]" means the total work in mJ observed when the 50:50 w/w combination of Polyquaternium-10 and Polyquaternium-47 is used at the 0.26% w/w concentration.
A Ratio value of greater than 1 indicates synergy between the two conditioning polymers, a Ratio value of less than 1 indicates antagonism between the two conditioning polymers, and a Ratio value equal to 1 indicates an additive effect of the two conditioning polymers.
The Ratio value for Example 3 is:

$$\text{Ratio} = \frac{[91.9/2] + [35.5/2]}{26.7} = 2.39$$

The Ratio value of 2.39 indicates synergy when ampholytic polymer Polyquaternium-47 and cationic polymer Polyquaternium-10 are used in combination in the shampoo formula of Example 3.

Examples 4–6

The following shampoo formulations demonstrate the synergistic benefit found when ampholytic polymer Polyquaternium-47 is used with cationic polymer guar hydroxypropyl trimonium chloride.

| Ingredient | INCI Name | % Active For Examples 4–6 | | |
|---|---|---|---|---|
| | | EX. 4 | EX. 5 | EX. 6 |
| Water | Water | q.s. to 100 for all | | |
| MERQUAT ® 2001[1] | Polyquaternium-47 | 0.26 | — | 0.13 |
| JAGUAR ® C-14S[2] | Guar Hydroxypropyl Trimonium Chloride | — | 0.26 | 0.13 |
| Standapol ® A[3] | Ammonium Lauryl Sulfate | 2.1 | 2.1 | 2.1 |
| Standapol ® EA-3[3] | Ammonium Laureth Sulfate | 4.7 | 4.7 | 4.7 |
| Tegobetaine ® L-7[4] | Cocamidopropyl betaine | 1.5 | 1.5 | 1.5 |
| Monamid ® 1113[5] | Cocamide DEA | 3.0 | 3.0 | 3.0 |
| Tween ® 20[6] | Polysorbate 20 | 1.0 | 1.0 | 1.0 |
| Citric Acid | Citric Acid | q.s. to pH 6.0 for all | | |
| Sodium Chloride | Sodium Chloride | 0.75 | 0.75 | 0.75 |
| MERGUARD ®[1] 1200 | Methyldibromo Glutaronitrile (and) Phenoxyethanol | 0.2 | 0.2 | 0.2 |

[1]From Calgon Corporation
[2]From Rhone-Poulenc
[3]From Henkel
[4]From Goldschmidt Chemical
[5]From Mona
[6]From ICI The shampoos from Examples 4–6 were evaluated for wet hair combing using the Dia-Stron Mini Tensile Tester, Dia-Stron Limited, Andover, Hampshire, U.K. The amount of work (mJ) required to comb the hair is measured directly. Lower work levels indicate superior conditioning as the hair is easier to comb.

| Shampoo | Total Work (mJ) |
|---|---|
| Example 4 | 35.5 |
| Example 5 | 38.4 |
| Example 6 | 26.3 |

The synergistic properties were evaluated by determining the reduction in total work found with the combination compared with what would be expected from each polymer individually. The Ratio value for Example 6 is:

$$\text{Ratio} = \frac{[38.4/2] + [35.5/2]}{26.7} = 1.38$$

The Ratio value of 1.38 indicates synergy when ampholytic polymer Polyquaternium-47 and cationic polymer guar hydroxypropyl trimonium chloride are used in combination in the shampoo formula of Example 6.

Examples 7–9

These examples are meant to demonstrate the efficacy of the polyampholyte conditioning agent and cationic polymer conditioning agent combination in a hand and body lotion emulsion. In the examples, Skin surface electrical impedance was measured using the Dermal Phase Meter (DPM) 9003 (Nova Technology Corporation, Portsmouth, N.H.) with DPM 9103 sensor probe. The probe is spring-loaded with a flat contact surface containing two concentric brass electrodes separated by a non conducting resin. The instrument models the stratum corneum as an alternating current circuit with a resistor and capacitor in parallel. The impedance measured, from an AC input, is based on the relationship of the resistance and the capacitance of the stratum corneum.

Capacitance is an electrical (or biophysical) property of the skin that provides insight into the level of hydration of the stratum corneum. The stratum corneum has a high electrical resistance by nature, which decreases when moisturized. The capacity of the conductor for instantaneous storage of an electrical charge provides the quantitative measurement. Hydration of the stratum corneum increases the capacitance so that more charge can be stored per unit volt. The greater the hydration, the greater the observed changes or differences between dry and moist skin. The DPM produces an impedance readout in DPM units which are directly related to the skin's electrical capacitance and indicates a relative value of moisturization of the skin.

The moisturization study was conducted on a 50 year old female subject. The panelist pre-washed the volar surfaces of both of her forearms with Ivory® soap, for five days prior to testing. All testing was done in a constant environment chamber at 22° C. and 50% RH. The panelist equilibrated for 30 minutes in the environmental chamber prior to application of the test emulsions. The DPM values were measured for each application site (baseline reading) immediately prior to applying 0.05g of the hand and body lotion to be tested. DPM readings were taken 15, 30, 60, 90 and 120 minutes after application. Results are expressed as Delta DPM, the difference between the measurements at each time interval and the baseline reading. Higher readings indicate higher moisture levels in the skin meaning better moisturization performance.

The polymer combinations were evaluated as part of the following hand and body lotion emulsion formula:

| Ingredients | Ex. 7 | Ex. 8 | Ex. 9 |
|---|---|---|---|
| Water | 85.3% | 85.3% | 85.9% |
| 45/45/10 m/m AA/MAPTAC/Methyl acrylate (b) | 0.3% | | |
| Polyquaternium 15 (c) | 0.3% | | |
| 80/20 w/w AA/DMDAAC copolymer (b) | | 0.3% | |
| Polymethacrylamidopropyltrimonium | | 0.3% | |

-continued

| | | | |
|---|---|---|---|
| chloride (c) | | | |
| Methyl Glucose Sesquistearate | 0.8% | 0.8% | 0.8% |
| PEG-20 Methyl Glucose Sesquistearate | 1.0% | 1.0% | 1.0% |
| Cetearyl Alcohol and Ceteareth-20 | 2.5% | 2.5% | 2.5% |
| Glyceryl Stearate | 1.5% | 1.5% | 1.5% |
| Mineral Oil | 8.0% | 8.0% | 8.0% |
| Preservative solution | 0.3% | 0.3% | 0.3% |

| Moisturization Results (Delta DPM Units): | | | | |
|---|---|---|---|---|
| 15 min | 30 min | 60 min | 90 min | 120 min |

| | 15 min | 30 min | 60 min | 90 min | 120 min |
|---|---|---|---|---|---|
| Example 7 | 55 | 43 | 31 | 34 | 27 |
| Example 8 | 102 | 68 | 51 | 47 | 47 |
| Example 9 | 16 | 19 | 16 | 16 | 12 |

(b) An ampholytic polymer according to the present invention.
(c) A cationic polymer according to the present invention.

The results indicate the superior moisturization effect of the compositions of the present invention (products of Examples 7 and 8).

What is claimed is:

1. A conditioning composition comprising:
   (a) about 5% to about 50%, by weight, of a surfactant component selected from the group consisting of anionic surfactants, amphoteric surfactants, cationic surfactants, nonionic surfactants, and zwitterionic surfactants;
   (b) about 0.05% to about 10%, by weight; of a water soluble, organic, ampholytic polymer conditioning agent
   (c) about 0.05% to about 10%, by weight, of a water soluble, organic, cationic polymer conditioning agent;
   (d) zero to about 70%, by weight, of a water insoluble liquid; and
   (e) an aqueous carrier
   wherein said ampholytic polymer conditioning agent of (b) is comprised of (A) at least one ethylenically unsaturated cationic monomer and (B) at least one ethylenically unsaturated acid containing monomer.

2. The conditioning composition of claim 1 wherein component (a) is in a concentration of about 5% to about 25% by weight.

3. The conditioning composition according to claim 2 wherein the composition contains both anionic and nonionic surfactants.

4. The conditioning composition according to claim 1 wherein the surfactant component of (a) is anionic.

5. The conditioning composition according to claim 1 wherein the surfactant component (a) is present in a concentration of about 5% to about 25% by weight, the ampholytic polymer conditioning agent (b) is present in a concentration of about 0.05% to about 7%, by weight, and the cationic polymer hair conditioning agent (c) is present in a concentration of about 0.05% to about 4%, by weight, all in an aqueous carrier (e).

6. The conditioning composition according to claim 5 wherein the surfactant component (a) is present in a concentration of about 10% to about 20% weight, the ampholytic polymer conditioning agent (b) is present in a concentration of about 0.05% to about 5% by weight, and the cationic polymer conditioning agent (c) is present in a concentration of about 0.05% to about 3%, by weight.

7. The conditioning composition according to claim 1 wherein said ampholytic polymer conditioning agent is comprised of (A) at least one ethylenically unsaturated cationic monomer, (B) at least one ethylenically unsaturated acid containing monomer, and (C) about 0 to about 80 mol % of a monomer that is an ethylenically unsaturated nonionic monomer.

8. The conditioning composition according to claim 7 wherein said ethylenically unsaturated acid containing monomer is selected from the group of acids consisting of carboxylic acids and sulfonic acids.

9. A conditioning composition according to claim 7, wherein said ampholytic polymer conditioning agent is comprised of:
   (A) about 1 to about 99 mol % of at least one monomer selected from the group consisting of alkyl acrylamidopropyl-dimethyl ammonium halides, alkyl methacrylamidopropyldimethyl ammonium halides, alkyl acryloyloxyethyl dimethyl ammonium halides, alkyl methacryloyloxyethyl dimethyl ammonium halides, and dialkyl diallyl ammonium halides;
   (B) about 1 to about 99 mol % of at least one monomer selected from the group consisting of acrylic acid (AA), methacrylic acid (MAA), 2-acrylamido-2-methylpropane sulfonic acid (AMPSA) 2-methacrylamido-2-methylpropane sulfonic acid (MAMPSA), n-methacrylamidopropyl,n,n-dimethyl, amino acetic acid, n-acrylamidopropyl,n,n-dimethyl, amino acetic acid, n-methacryloyloxyethyl,n,n-dimethyl,amino acetic acid, and n-acryloyloxyethyl,n,n-dimethyl,amino acetic acid; and
   (C) about 0 to about 80 mol % of at least one monomer selected from the group consisting of $C_1$–$C_{22}$ straight or branched chain alkyl acrylate or methacrylate, a $C_1$–$C_{22}$ straight or branched chain n-alkyl acrylamide or methacrylamide, acrylamide methylacrylamide, n-vinylpyrrolidone, vinyl acetate or ethoxylated and propoxylated acrylate or methacrylate; with a weight average molecular weight of, as determined by viscometry, from about 100,000, to about 10,000,000.

10. The conditioning composition according to claim 9 wherein (C) is present in the ampholytic polymer in a concentration of about 1 to about 40 mol % and is at least one monomer selected from the group consisting of $C_1$–$C_{22}$ acrylate esters, $C_1$–$C_{22}$ methacrylate esters, acrylamide, and $C_1$–$C_{22}$ n-alkyl acrylamides.

11. The conditioning composition according to claim 10 wherein said $C_1$–$C_{22}$ acrylate esters are selected from the group consisting of methyl, ethyl, butyl, octyl, lauryl, and stearyl acrylate esters, said $C_1$–$C_{22}$ methacrylate esters are selected from the group consisting of methyl, ethyl, butyl, octyl,lauryl, and stearyl methacrylate esters, and said $C_1$–$C_{22}$ n-alkyl acrylamide are selected from the group consisting of n-methyl, n-ethyl, n-butyl, n-octyl, t-octyl, n-lauryl, and n-stearyl acrylamides and methacrylamides.

12. The conditioning composition according to claim 9 wherein the monomers of (A) are selected from the group consisting of MAPTAC, APTAC, AETAC, METAC, METAMS and DMDAAC and the monomers from the (B) are selected from the group consisting of acrylic acid, methacrylic acid, and AMPSA.

13. The conditioning composition according to claim 1 further comprising a silicone conditioning agent and about 0.05 to about 5% by weight of an organic water insoluble liquid selected from the group consisting of hydrocarbon oils, fatty esters having 10 to 22 carbon atoms, and mixtures thereof.

14. The conditioning composition according to claim 13 wherein said anionic surfactant of (a) is selected from the group consisting of lauryl sulfate, lauryl ether sulfate, α-olefin sulfonates, and their ammonium, sodium and amine salts; said nonionic surfactant of (a) is selected from the group consisting of fatty di or mono ethanol amides, mono or di fatty esters of polyethylene or polypropylene glycol, and mono or di fatty esters of $C_1$–$C_6$ glycols; and the silicone conditioning agent is selected from the group consisting of dimethicone, cyclomethicone, trimethyl silyl amodimethicone, phenyl trimethicone, trimethyl siloxy silicate, polyorganosiloxane, polyalkylsiloxane, polyarylsiloxane, polyalkarylsiloxane, and polyestersiloxane copolymers.

15. The conditioning composition according to claim 1 wherein said ampholytic polymer and cationic polymer conditioning agents exists in a complex coacervate form upon dilution of the components (a), (b), and (c) with water at a water:shampoo composition weight ratio of 20:1.

16. A method for treating a keratin based substrate comprising contacting said substrate with the composition of claim 1.

17. A conditioning composition comprising:
   (a) about 5% to about 50%, by weight, of a surfactant component selected from the group consisting of anionic surfactants, amphoteric surfactants, cationic surfactants, nonionic surfactants, and zwitterionic surfactants;
   (b) about 0.05% to about 10%, by weight; of a water soluble, organic, ampholytic polymer conditioning agent
   (c) about 0.05% to about 10%, by weight, of a water soluble, organic, cationic polymer conditioning agent;
   (d) zero to about 70%, by weight, of a water insoluble liguid; and
   (e) an aqueous carrier
      wherein said water soluble, organic ampholytic polymer conditioning agent of (b) is comprised of:
      (A) about 1 to about 99 mol % of at least one monomer selected from the group consisting of alkyl acrylamidopropyl-dimethyl ammonium halides, alkyl methacrylamidopropyldimethyl ammonium halides, alkyl acryloyloxyethyl dimethyl ammonium halides, alkyl methacryloyloxyethyl dimethyl ammonium halides, and dialkyl diallyl ammonium halides;
      (B) about 1 to about 99 mol % of at least one monomer selected from the group consisting of acrylic acid (AA), methacrylic acid (MAA), 2-acrylamido-2-methylpropane sulfonic acid (AMPSA) 2-methacrylamido-2-methylpropane sulfonic acid (MAMPSA), n-methacrylamidopropyl,n,n-dimethyl,amino acetic acid, n-acrylamidopropyl,n, n-dimethyl,amino acetic acid, n-methacryloyloxyethyl,n,n-dimethyl, amino acetic acid, and n-acryloyloxyethyl,n,n-dimethyl,amino acetic acid; and
      (C) about 0 to about 80 mol % of at least one monomer selected from the group consisting of C1–C22 straight or branched chain alkyl acrylate or methacrylate, a C1–C22 straight or branched chain n-alkyl acrylamide or methacrylamide, acrylamide methylacrylamide, n-vinylpyrrolidone, vinyl acetate or ethoxylated and propoxylated acrylate or methacrylate; with a weight average molecular weight of, as determined by viscometry, from about 100,000, to about 10,000,000
      wherein the mol ratio of (A):(B) in said water soluble, organic ampholytic polymer conditioning agent ranges from about 25:75 to about 75:25.

18. The conditioning composition according to claim 17 wherein at least one monomer from (A) is present in a mol ratio to at least one monomer from (B) at ratio (A):(B) of 25:75 to 75:25, and at least one monomer from (C) is present in an amount of about I to about 35 mol %.

19. The conditioning composition according to claim 18 wherein said ampholytic polymer conditioning agent of (b) is selected from the group of polymers consisting of; (1) a polymer comprised of about 45 mol % MAPTAC, about 45 mol % acrylic acid, and about 10 mol % methylacrylate; and (2) a polymer comprised of about 30 mol % DMDAC, about 35 mol % acrylic acid, and about 35 mol % acrylamide: and wherein said cationic polymer conditioning agent of (c) is selected from the group of polymers consisting of; (1) the polymeric quaternary ammonium salts of hydroxyethyl cellulose reacted with a trimethyl ammonium substituted epoxide; (2) the quaternary ammonium derivatives of hydroxypropyl guar; and (3) the quaternary ammonium derivatives of starches.

20. A method for treating hair comprising contacting hair with the composition of claim 19 wherein (a) contains 15 weight % anionic surfactant and about 1 to 2 weight % nonionic surfactant, (b) contains about 0.05 to 1.5% ampholytic polymer conditioning agent, and (c) contains about 0.05 to 0.4 weight percent of said cationic polymer conditioning agent.

* * * * *